United States Patent
Baer et al.

(10) Patent No.: US 7,298,490 B2
(45) Date of Patent: Nov. 20, 2007

(54) HYDROGEN SENSOR BASED UPON QUADRUPOLE ABSORPTION SPECTROSCOPY

(75) Inventors: Douglas S. Baer, Menlo Park, CA (US); Manish Gupta, Mountain View, CA (US); Thomas Owano, Mountain View, CA (US); Anthony O'Keefe, Cupertino, CA (US)

(73) Assignee: Los Gatos Research, Mountain View, CA (US)

( * ) Notice: Subject to any disclaimer, the term of this patent is extended or adjusted under 35 U.S.C. 154(b) by 130 days.

(21) Appl. No.: 11/240,190

(22) Filed: Sep. 30, 2005

(65) Prior Publication Data

US 2007/0076209 A1    Apr. 5, 2007

(51) Int. Cl.
*G01B 9/02* (2006.01)
*G01J 3/45* (2006.01)

(52) U.S. Cl. ..................... 356/454; 356/519
(58) Field of Classification Search ............. 356/451, 356/454, 519
See application file for complete search history.

(56) References Cited

U.S. PATENT DOCUMENTS 4,535,241 A * 8/1985 Eberhardt ............. 250/339.13
6,795,190 B1 * 9/2004 Paul et al. ................. 356/437
6,839,140 B1 * 1/2005 O'Keefe et al. ............ 356/436
7,054,008 B2 * 5/2006 Wang et al. ................ 356/437

OTHER PUBLICATIONS

Uwe Fink et al., "Frequency and Intensity Measurements on the Quadrupole Spectrum of Molecular Hydrogen", Journal of Molecular Spectroscopy, vol. 18, 1965, pp. 384-395.
G.C. Bjorklund et al., "Frequency Modulation (FM) Spectroscopy", Applied Physics B, vol. 32, 1983, pp. 145-152.
J. Michael Shull, "$H_2$ Resonance Fluorescence with Lyman-$\alpha$", Astrophysical Journal, vol. 224, Sep. 15, 1978, pp. 841-847.

* cited by examiner

*Primary Examiner*—Michael A. Lyons
(74) *Attorney, Agent, or Firm*—Schneck & Schneck; Thomas Schneck; Mark Protsik

(57) ABSTRACT

The disclosure describes an absorption spectroscopy method for sensing hydrogen gas in a sample atmosphere and an associated hydrogen sensor. A light beam, having a wavelength corresponding to a vibrational transition of hydrogen molecules from a ground vibration state to any excited rotational vibration state via a quadrupole interaction, is introduced into an optical cavity adapted to receive a sample atmosphere to be tested for the presence of hydrogen gas. The light is introduced into the cavity in an off-axis alignment to systematically eliminate cavity resonances, while preserving the absorption signal amplifying properties of such cavities. Hydrogen absorption is measured is terms of cavity output, as in the ICOS technique.

14 Claims, 2 Drawing Sheets

Fig._1

HYDROGEN SENSOR BASED UPON QUADRUPOLE ABSORPTION SPECTROSCOPY

TECHNICAL FIELD

The present invention relates to hydrogen sensors for detecting the presence and/or measuring the concentration of hydrogen gas, especially in environments containing other gases. The present invention also relates to practical applications of absorption spectroscopy methods and apparatus, especially ones adapted for integrated cavity output spectroscopy (ICOS).

BACKGROUND ART

Detection of any leakage of gaseous hydrogen (GH2) from hydrogen-fueled vehicles is critical in preventing the accumulation of flammable and explosive concentrations of this gas. Concentrations of GH2 greater than or equal to approximately 4% in air are flammable and can be explosive. GH2 leakage detection will also be of great importance for safety in transport and storage in the emerging hydrogen fuel-celled infrastructure. In hydrogen-fueled launch vehicles, during cryogenic storage and subsequent transport of liquid hydrogen, leaks can occur that are associated with the failure of sealed connections at the low temperatures required.

The standard method for the detection of leaks is the use of mass spectrometers. Mass spectrometers have sufficient chemical specificity detection capability to allow detection of leaking amounts of GH2 as opposed to detection of other atmospheric contaminants, such as oxygen, nitrogen, carbon disulfide, carbon monoxide, and methane that exist in an operating environment. However, mass spectrometers have a relatively slow response time in detection of leaking GH2 when applied to large vehicles, such as liquid motor rockets, and are expensive to purchase and to operate.

A widely used alternative in the detection of GH2 is the palladium based sensor approach. Most palladium sensors are based on reversible changes in the physical or electronic properties of palladium in the presence of GH2 or are based on use of palladium as a catalyst for certain reversible chemical reactions in detection of GH2. The limitations of these palladium type sensors arise from the slow time response of the sensor, typically minutes, and the sensitivity to other external environmental factors such as temperature.

It would be useful to provide a GH2 sensor that has sufficient chemical specificity capability, as well as a fast response, and is capable of operating for long periods of time without the need for repairs, recalibration, or replacement. A sensor scheme based upon optical absorption would provide the required sensitivity and specificity. J. Michael Shull (in Astrophysical Journal, vol. 224, pages 841-847, 1978) demonstrated a scheme employing H2 resonance fluorescence with Lyman alpha light (121.567 nm). The major limitation with this approach is that the extreme ultraviolet light employed is strongly attenuated in air, and in the presence of GH2 could even stimulate the explosive chemical reactions that are sought to be avoided, so there can be no other gases present in the test region. This is a significant limitation in the general utility of the invention.

Integrated Cavity Output Spectroscopy (ICOS) methods and associated instruments employ optical absorption cells for spectroscopic purposes. These spectroscopy methods and instruments have a broad range of other applications, such as characterizing mirror reflectivities, determining optical cavity losses (including scattering, absorption, etc.) and measuring thin film absorption. This technique can also be used in the detection of various chemical species. The ICOS method has been used for the detection of trace concentrations of various gas-phase chemical species by measuring the wavelength resonant absorptions that arise from the electronic and vibrational structure of the chemical.

However, the detection of gaseous hydrogen molecules using optical absorption spectroscopy methods such as ICOS has been unsuccessful to date, since there are no easily accessed electronic states to probe and since there is no strong vibrational transition to use as a probe since these are all forbidden for a homonuclear diatomic molecule. Uwe Fink, T. A. Wiggins, and D. H. Rank (Journal of Molecular Spectroscopy, Vol. 18, pages 384-395, 1965) identify specific transition frequencies and absorption line strengths of hydrogen that are extremely weak and not feasible to use as a diagnostic probe using conventional absorption spectroscopy.

Since the hydrogen line widths are broadened due to the Doppler broadening of this light molecule, other sensitive techniques such as frequency modulation (cf., G. C. Bjorklund, M. D. Levenson, W. Lenth, and C. Oritz, "Theory of lineshapes and signal-to-noise analysis", Appl. Phys. B, vol. 32, page 145 (1983)) are not viable solutions to the problem.

DISCLOSURE

The solution represented by the present invention utilizes extremely weak, quantum mechanically forbidden, vibration-vibration transitions of the hydrogen molecule along with the extremely sensitive off-axis ICOS detection scheme to provide accurate and fast detection of molecular GH2 over a range of concentrations important to many applications (0.1%-100%). There are three vibrational transitions that might be utilized in a hydrogen sensor. These all originate in the ground vibrational state of the molecule, and from one of the lowest populated rotational levels. The absorptions connect the ground vibrational state to either the first excited vibrational level, $v=1$; to the second excited vibrational level, $v=2$; or to the third excited vibrational level, $v=3$. Since these transitions are forbidden for dipole radiation, it must occur through the very weak quadrupole interaction. This reduces the absorption strength of these transitions so that they are only seen when extremely long absorption paths are used. The quadrupole allowed transitions must have a change in rotational level of either 0 or 2 quantum units. The individual transition lines are designated as either Q transitions or as S transitions, respectively. The specific transitions are listed in Table 1 (data taken from the aforementioned Fink et al paper), where the vibrational transition, Q or S designation, transition frequency (wavenumber in $cm^{-1}$), and integrated absorption line strength ($cm^{-2} \cdot amagat^{-1}$) are given. [Note: An "amagat" is a dimensionless quantity $\rho_{rel}$ expressing the measured gas density relative to the corresponding gas density at standard temperature and pressure (STP), i.e., at 0° C. or 273.15 K, and 1 atm or 101.325 kPa; $\rho_{rel} = \rho_{measured}/\rho_{STP}$. Based on standard values for an ideal gas, 1 amagat is equivalent to about $2.6868 \times 10^{19}$ molecules/$cm^3$ or 44.615 mol·$m^{-3}$. Hydrogen has a density under STP conditions of $8.987 \times 10^{-2}$ kg·$m^{-3}$.]

TABLE 1

| Vibration Band | Line Designation | Frequency | Absorption Strength In units of $\Delta v/cm/Amagat$ |
|---|---|---|---|
| 1-0 band | Q(1) | 4155.2575 | 4.5 * 10(−7) |
|  | Q(2) | 4143.4668 | 6.5 * 10(−8) |
|  | Q(3) | 4125.8718 | 4.4 * 10(−8) |
|  | S(0) | 4497.8385 | 2.8 * 10(−7) |
|  | S(1) | 4712.9085 | 9.0 * 10(−7) |
|  | S(2) | 4917.0118 | 1.4 * 10(−7) |
|  | S(3) | 5108.4066 | 8.4 * 10(−8) |
| 2-0 band | Q(1) | 8075.3105 | 7.8 * 10(−8) |
|  | S(1) | 8406.3010 | 1.4 * 10(−7) |
|  | S(2) | 8604.2224 |  |
|  | S(3) | 8785.4800 |  |
| 3-0 band | Q(1) | 11764.948 | 1.3 * 10(−8) |
|  | S(0) | 12084.651 |  |
|  | S(1) | 12265.543 |  |
|  | S(2) | 12424.443 |  |

An optical absorption technique to determine the concentration of GH2 must be able to detect a change in transmitted optical signal. For example, at the threshold for combustion in air of 4% hydrogen concentration, the (2-0) band Q(1) line will produce, at 1 atmosphere pressure and 273 degrees Kelvin, an attenuation of a resonant laser beam of 0.000427% when the light is passed through a 100 cm length sample of the gas. Under these important combustion point conditions, this line has a very weak absorption and cannot be easily measured using conventional techniques. None of the other lines offer much better attenuation.

However, by employing the off-axis ICOS technique, we can increase the effective path length of the sample gas by a factor of from 100 to 100,000. Operating, for example, at a laser frequency of 8075.31 cm$^{-1}$ (near 1238 nm wavelength) corresponding to the (2-0) band Q(1) line, and using ICOS mirrors with a reflectivity of 99.995%, we can achieve absorption of 8.5%. The ICOS technique has demonstrated the sensitivity to measure effective attenuations as low as 0.01%, so the above ICOS system will be capable of measuring GH2 as low as 0.0005% fractional concentration.

The absorption spectroscopy hydrogen sensor apparatus may be an ICOS instrument like that described in U.S. Pat. No. 6,795,190, with off-axis light insertion into the optical cavity. Paul, Scherer, and O'Keefe (U.S. Pat. No. 6,795,190 B1) describe a method by which very weak optical attenuations can be amplified by making the measurement inside an optical cavity comprised of two or more highly reflecting mirrors. In order to serve as a hydrogen sensor, the optical cavity should be able to receive a sample atmosphere to be tested for the presence of hydrogen gas, and also the light beam should have a wavelength corresponding to one of the vibrational transitions of hydrogen molecules from a ground vibration state to any excited rotational vibration state via a quadrupole interaction, as just described.

It may be useful, but not essential, to confine the sample gas to a sample cell that can be maintained at a reduced pressure (0.1 to 0.5 atmosphere), particularly for the (3-0) band lines to reduce the interference of nearby water absorption lines as well as to increase the sample flow rate. However, the hydrogen line width is dominated by the Doppler width and so reduced pressure has little effect upon the actual measurement. A free standing cavity within an ambient environment is generally adequate to detect GH2 within this environment.

DETAILED DESCRIPTION

Figure 1:
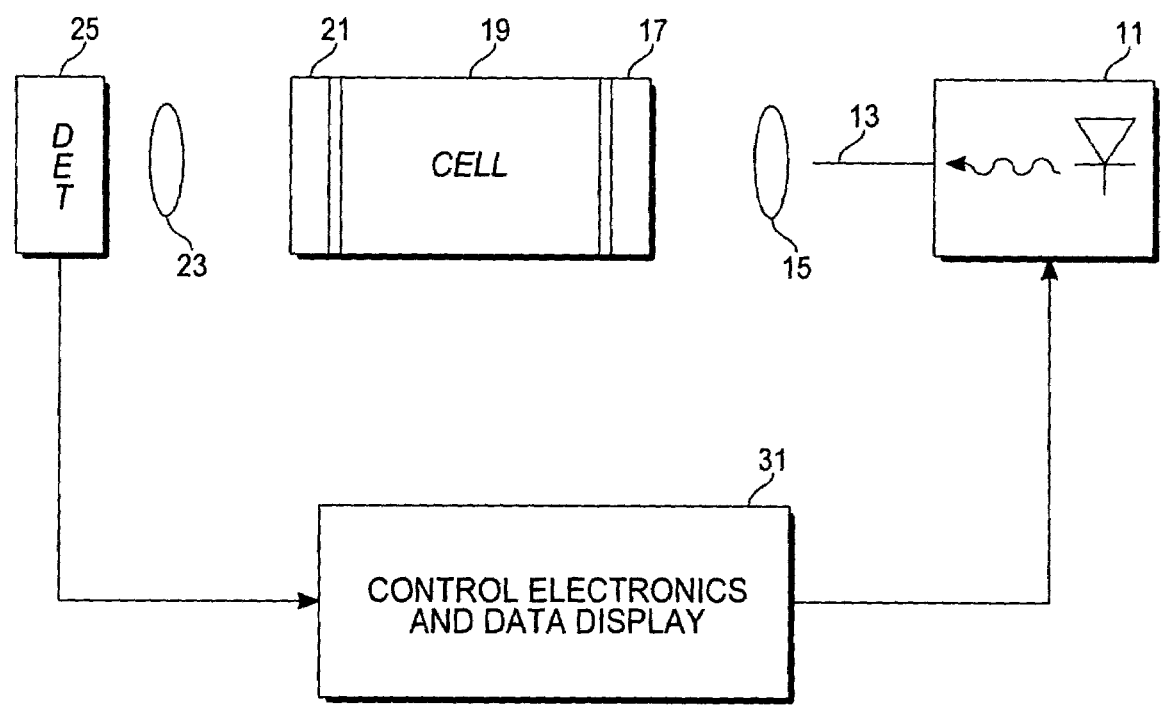
FIG. 1 is a schematic perspective view of an apparatus employing off-axis light injection into an optical cavity according to the present invention.

With reference to FIG. 1, a hydrogen sensor apparatus employing off-axis light injection into an optical cavity (defined between mirrors 17 and 21) is seen. A diode laser 11 produces light that can be tuned on and off the weak hydrogen absorption resonance. This light can be delivered to the sample gas cell 19 by means of a short fiber optic strand 13. The light is coupled into the sample cell 19 using a lens 15. The sample cell 19 is fitted with at least two mirrors 17 and 21 aligned so that the light coupled into the cell 19 is trapped inside the cell, resulting in a long effective path length. The light is injected into the sample cell by passing the light emerging from the fiber optic 13 through the first highly reflecting mirror 17. The mirrors 17 and 21 can be dielectric multi-layer coating mirrors that are designed to have a high reflectivity at the wavelength corresponding to the laser light and the weak hydrogen absorption. Most of the light is reflected away from the cell 19, however a small fraction passes into the cell 19 and is trapped by the highly reflective mirrors 17 and 21. Over time, the light slowly leaks out and is collected using a second lens 23 and measured by a sensitive detector 25. The detector signal is sent to the control electronics 31 where the absorption signal is processed and the results displayed. The control electronics 31 also controls the laser power and sweeping of the laser wavelength across a selected absorption line of hydrogen. The OA-ICOS design employed by this apparatus results in a very long effective path length in which the weak hydrogen absorption grows to a level easily measured. A small mechanical pump can be employed to draw the sample gas through the cell 19. Alternatively, the mirrors 17 and 21 could define a free-standing cavity without a sample cell, with gas from the ambient environment simply being present between the mirrors. The ambient environment could be circulated near the apparatus, or generally, using a fan.

To demonstrate feasibility of the invention, we applied an off-axis ICOS strategy, preferably like that described in U.S. Pat. No. 6,795,190, for determination of hydrogen concentrations in a test cell where the concentration of hydrogen was varied from 1% to 100% in air. The laser wavelength was 1238 nm and was tuned rapidly over the hydrogen (2-0) Q(1) line. A line within the (2-0) band was chosen for convenience because it is easy to obtain good outputs from laser diodes and efficient detectors at the required near IR frequencies. Longer wavelength lasers for detecting lines in the (1-0) band are presently not very efficient. Also, the lines in the (3-0) band are very close to $H_2O$ absorption lines and may overlap at ambient temperatures and pressures, necessitating a low-pressure sample cell. Nevertheless, any of the lines in the (1-0), (2-0) and (3-0) bands are detectable using the present invention.

The data summarized in Table 1 give the integrated absorption strength for this particular (2-0) Q(1) transition as $7.8 \times 10^{-8}$ $\Delta v$-cm$^{-1}$-amagat$^{-1}$., where $\Delta v$ is in units of inverse centimeters. To convert this value into a useful estimate of the actual absorption expected for a given GH2 concentration, sample cell length, and cavity mirror reflectivity (effective gain) we need to estimate the width of the absorption line. The best estimate is the Doppler width, $\Gamma$, which for hydrogen at this wavelength is approximately 0.073 cm$^{-1}$. The calculation of the fractional absorption is:

$$I/I_o = \exp[-(A_o \times L \times \rho/\Gamma)],$$

where $A_o$ is the integrated absorption coefficient from Table 1, L is the length of the sample cavity, $\rho$ is the sample hydrogen density expressed in amagat, and $\Gamma$ is the Doppler width in wave numbers (0.073 cm$^{-1}$). In this example we have assumed a 0.118 amagat concentration of hydrogen in an air atmosphere sample at 294 degrees Kelvin, and a sample cell length of 83 cm.

We can calculate the predicted absorption for the assumed conditions $$I/I_o = \exp[-(A_o \times \rho \times L/\Gamma)]$$
$$= \exp[-(7.8 \times 10^{-8} \Delta v - cm^{-1} - amagat^{-1} \times 0.118 \, amagat \times 83 \, cm/0.073 \, cm^{-1})]$$

and the fraction absorbed per pass is $$= 1.046 \times 10^{-5}.$$

This number represents the single pass fractional attenuation of the laser beam as it traverses the sample cell. This is a very small attenuation and cannot be easily measured using conventional methods.

When light used to make the absorption measurement is properly directed, the effective cavity FSR is made significantly smaller than the laser (or other light source) linewidth, and effects due to cavity resonances are suppressed and the energy coupled into the cavity is no longer a function of the light wavelength. In this limit, the cavity behaves like an optical cell with an effective path length $L_{eff}=L/(1-R)$, where L is the distance between the cavity mirrors. For the values of our test, with L=0.83 meters, R=0.9999506, $L_{eff}$=16,800 meters. The transmitted laser intensity I through an empty cavity may be expressed:

$$I = \frac{I_L C_p T}{2(1-R)}(1 - \exp(-t/\tau)), \quad (1)$$

$$\text{where } \tau = \frac{L/c}{1-R}$$

and $I_L$ is the incident laser intensity, $C_p$ is a cavity coupling parameter, R and T are the mirror intensity reflection and transmission coefficients, $\tau$ is the characteristic cavity decay (ringdown) time and c is the speed of light. When the laser (or other light source) is switched on, the laser intensity in the cavity increases with a characteristic time constant $\tau$, also known as the 'ring-down' time. Steady-state in the cavity is reached when $I = I_L C_p T/(2(1-R))$. Once sufficient optical power is leaving the cavity, the light source can be interrupted to observe the ringdown decay. As the intensity buildup occurs predictably and on a well-defined timescale, this can be done with a simple mechanical chopper or by simply turning off the light source. The ringdown decay $\tau$ may be routinely recorded (at any time) to monitor the path length $L_{eff}$ in the cavity with the laser tuned to a non-absorbing wavelength i.e., 'off line', or in an empty cavity. With an absorbing gas between the mirrors, R is replaced by R', given by:

$$R' = R \cdot \exp(-\alpha(\omega)), \quad (2)$$

where $\alpha(\omega)$ represents the absorbance of the gas over the length of the cavity. Comparing Eq. (2) with the Beer-Lambert absorption formula for a single pass ($I/I_o=\exp(-\alpha(\omega))$) reveals that $I/I_o=R'/R$. Thus Equations (1) and (2) indicate that essential absorption information is contained in the steady-state cavity output intensity, which is the basis for this technique. The change in steady-state cavity output due to the presence of an absorbing species is given by $$\frac{\Delta I}{I} = \frac{GA}{1+GA}, \quad (3)$$

where the single-pass absorption is A, equal to $$1 - I/I_o = \exp[-(A_o \times \rho \times L/\Gamma)] \quad (4)$$

and $G = R/(1-R)$. For weak absorption (GA<<1), the cavity provides a linear absorption signal gain, given by G. Physically, G equals the number of optical passes occurring within cavity decay time. Using equation 3, and taking the cavity mirror reflectivity to be 99.99506%, i.e. a Gain of 20,243 and the per-pass absorption of $1.046 \times 10^{-5}$ we get a net fractional absorption of:

$$\frac{\Delta I}{I} = \frac{GA}{1+GA}, = 0.1747, \text{ or } \sim 17.47\%.$$

The density of hydrogen used in the above example corresponds to a fractional content (at standard temperature and pressure) of 11.8% fractional concentration, or about 3 times the combustion threshold in air. This demonstrates that the approach we have developed can be especially useful in the detection and monitoring of hydrogen over the concentration range of interest for warning of fire and explosion danger. Because the approach is extremely fast, it can be a significant improvement over existing technologies.

Figure 2:
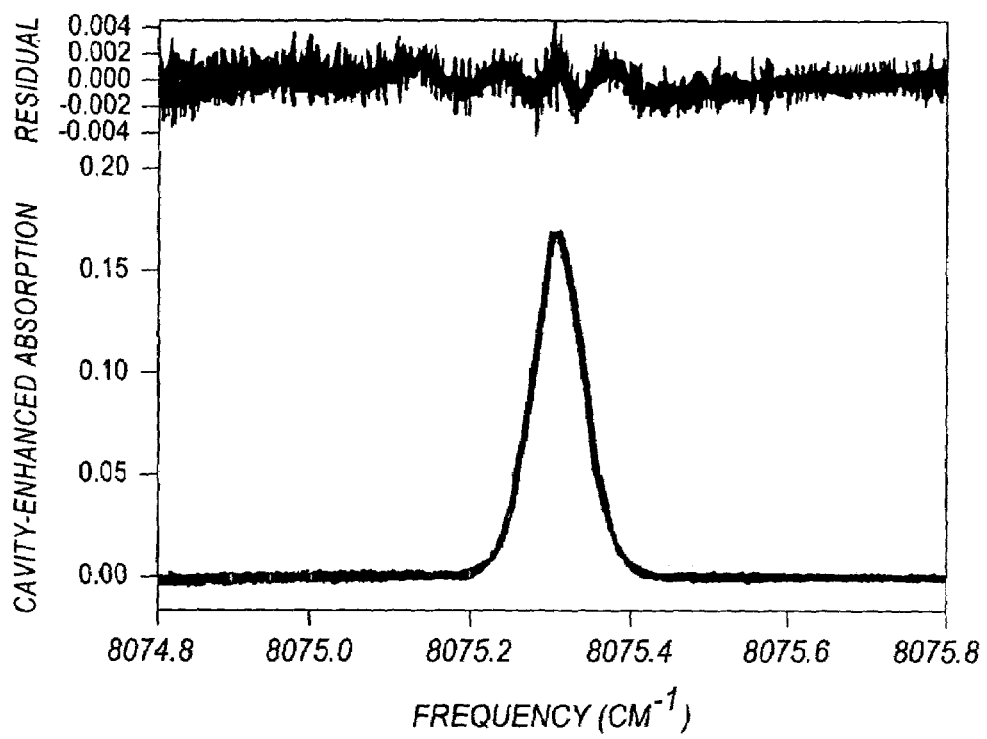
FIG. 2 is a graph of measured cavity output versus laser wavelength using the apparatus of FIG. 1 with a light-absorbing sample present in the cavity (a rotationally resolved line of the molecular hydrogen quadrupole band near 1238 nm wavelengths is shown), as measured in an integrated cavity output mode. The hydrogen density was 0.113 amagat.
Figure 3:
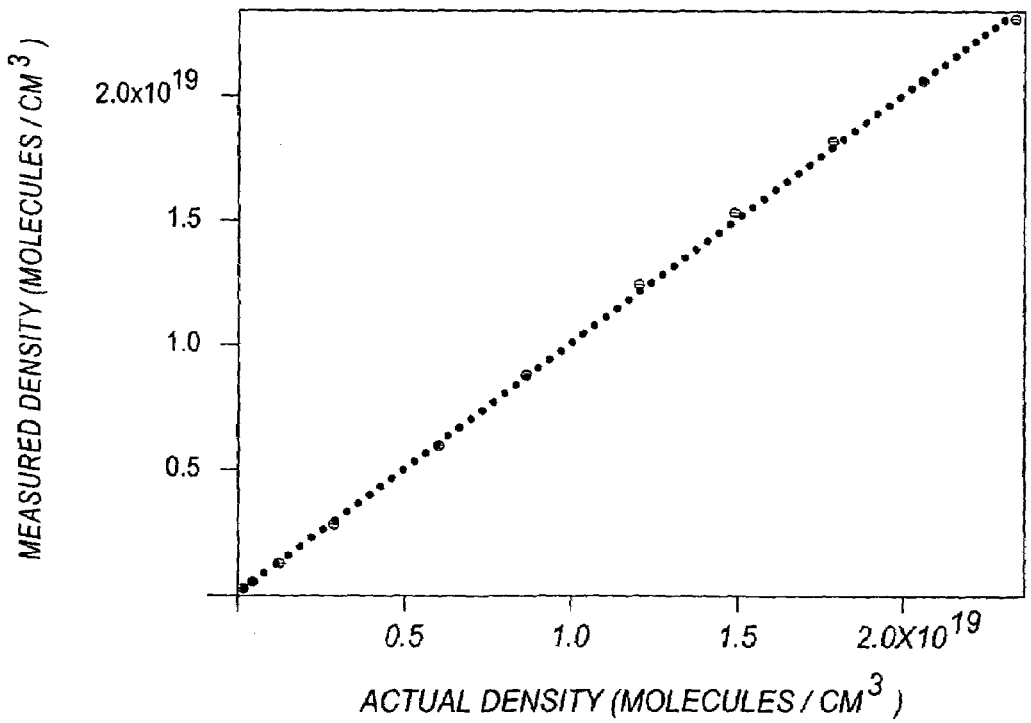
FIG. 3 shows the measured ICOS signal as a function of hydrogen concentration over the range from 1% hydrogen in air, to 100% hydrogen, using mirrors of 99.995% reflectivity at 1238 nm wavelength.

With reference to FIG. 2, using the above-described hydrogen sensor apparatus in an integrated cavity output mode, the output intensity is measured in the vicinity of 1238 nm wavelength with a gaseous sample present in the cavity. A (2-0), Q(1) absorption line of molecular hydrogen is observed against a baseline background. The measurements correspond to a Voight profile fit assuming the known absorption of the line at the pressure and density of the test and a path length of 16,800 meters. The difference between the measured spectra and the fit is shown above the main graph. The hydrogen gas density in the sample cell was 0.118 Amagat. In FIG. 3, the measured ICOS signal as a function of hydrogen concentration is shown over a range from 1% to 100% hydrogen in air. This assumes a cavity mirror reflectivity of 99.99497%.

The invention claimed is:

1. An absorption spectroscopy hydrogen sensor, comprising:
   an arrangement of two or more mirrors forming a stable optical cavity, the cavity mirror arrangement defining an axial light path in the resonant cavity wherein each reflection at each mirror thereof occurs at substantially the same spot for said axial light path, the cavity mirror arrangement also defining off-axis light paths in the optical cavity wherein successive reflections at any given mirror thereof occur at different locations for any off-axis light path, the cavity adapted to receive a sample atmosphere to be tested for the presence of hydrogen gas;
   a light source providing a light beam that is introduced into the optical cavity through a partially transmissive mirror of the cavity, the light beam being directed along any off-axis light path in the optical cavity, the light beam having a wavelength corresponding to a vibrational transition of hydrogen molecules from a ground vibration state via a quadrupole interaction to any excited rotational vibration state;
   a detector situated in a position to receive and measure a portion of the light beam from the resonant cavity; and
   means for processing data representing the light measurement from the detector for analyzing a sample received by said optical cavity.

2. The hydrogen sensor as in claim 1, wherein the wavelength of the light beam is near 1238 mm, corresponding to a (2-0) vibration band, Q(1) transition line of molecular hydrogen.

3. The hydrogen sensor as in claim 1, wherein the wavelength of the light beam overlaps any hydrogen quadrupole transition corresponding to a (1-0), (2-0), or (3-0) vibration band of molecular hydrogen.

4. The hydrogen sensor as in claim 1, wherein the light source is any wavelength tunable light source producing a measurable transmitted signal, and the sensor further comprises:
   means for tuning the wavelength of the light beam introduced from the source into the optical cavity across a selected quadrupole transition wavelength to obtain, from the transmitted light measurement of the detector, both baseline absorption in the vicinity of the transition wavelength and an absorption signal at the transition wavelength in the presence of any hydrogen gas for a sample received within the optical cavity.

5. The hydrogen sensor as in claim 1, wherein the optical cavity includes a low-scatter sample gas flow arrangement passing through the off-axis light paths of the cavity for measurement of hydrogen gas in the sample gas flow.

6. The hydrogen sensor as in claim 1, wherein the optical cavity is situated in an ambient environment for sensing any hydrogen gas in said ambient environment.

7. An absorption spectroscopy method of sensing hydrogen gas, comprising:
   injecting a light beam into an arrangement of mirrors that is arranged to form a stable optical cavity, the light beam being introduced through a partially transmissive mirror into the optical cavity along any off-axis light path thereof wherein successive reflections at any given mirror of the optical cavity occur at different locations on that mirror, the light beam having a wavelength corresponding to a vibrational transition of hydrogen molecules from a ground vibration state via a quadrupole interaction to any excited rotational vibration state, the optical cavity adapted to receive a sample atmosphere to be tested for the presence of hydrogen gas;
   measuring light from the optical cavity to obtain light measurement data, including cavity output intensity data representing a measure of optical absorption by any hydrogen gas present in the sample atmosphere; and
   processing the light measurement data, including the cavity output intensity data, to obtain an analysis of the sample atmosphere received by the optical cavity, the analysis including at least a real-time indication of a detection of presence of hydrogen gas in the sample atmosphere at fractional concentrations below 4%.

8. The method as in claim 7, wherein the wavelength of the light beam is near 1238 nm, corresponding to a (2-0) vibration band, Q(1) transition line of molecular hydrogen.

9. The method as in claim 7, wherein the wavelength of the light beam overlaps any hydrogen quadrupole transition corresponding to a (1-0), (2-0), or (3-0) vibration band of molecular hydrogen.

10. The method as in claim 7, further comprising tuning the wavelength of the light beam across a selected quadrupole transition wavelength to obtain both baseline absorption in the vicinity of the transition wavelength and an absorption measurement at the transition wavelength associated with the presence of hydrogen gas.

11. The method as in claim 7, wherein a low-scatter sample gas flow configuration directing a flow of sample gas across the off-axis light paths of the light beam within the optical cavity.

12. The method as in claim 7, wherein the optical cavity is situated in an ambient environment for sensing any hydrogen gas in said ambient environment.

13. The method as in claim 7, wherein the analysis further reports a measurement of the fractional concentration of hydrogen gas in the sample atmosphere.

14. The method as in claim 7, wherein detection of hydrogen gas in the sample atmosphere is obtained from the cavity output intensity data at fractional concentrations as low as 0.0005% hydrogen.

* * * * *